US009301726B2

(12) United States Patent
Mackie et al.

(10) Patent No.: US 9,301,726 B2
(45) Date of Patent: Apr. 5, 2016

(54) CT MACHINE FOR MULTI-ANGLE SCANNING OF STATIONARY PATIENTS

(71) Applicant: Wisconsin Alumni Research Foundation, Madison, WI (US)

(72) Inventors: Thomas Mackie, Verona, WI (US); George Petry, Madison, WI (US); Peter Muir, Madison, WI (US); Mark Markel, Middleton, WI (US); Robert Swader, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 71 days.

(21) Appl. No.: 14/268,539

(22) Filed: May 2, 2014

(65) Prior Publication Data
US 2015/0313557 A1    Nov. 5, 2015

(51) Int. Cl.
*A61B 6/00* (2006.01)
*A61B 6/03* (2006.01)
*A61N 5/10* (2006.01)
*H05G 1/02* (2006.01)

(52) U.S. Cl.
CPC .............. *A61B 6/4429* (2013.01); *A61B 6/035* (2013.01); *A61B 6/4458* (2013.01); *A61B 6/508* (2013.01); *A61N 5/1083* (2013.01); *H05G 1/02* (2013.01); *A61N 5/1049* (2013.01)

(58) Field of Classification Search
CPC .............. A61B 6/00; A61B 6/02; A61B 6/03; A61B 6/032; A61B 6/035; A61B 6/04; A61B 6/10; A61B 6/102; A61B 6/107; A61B 6/44; A61B 6/4411; A61B 6/4429; A61B 6/4435; A61B 6/4447; A61B 6/4458; A61B 6/4464; A61B 6/508; A61B 6/547; A61B 6/58; A61B 6/589; A61N 5/10; A61N 5/1048; A61N 5/1049; A61N 5/1056; A61N 5/1059; A61N 5/1077; A61N 5/1081; A61N 5/1083; A61N 5/1092; A61N 5/1094; G05B 2219/40; G05B 2219/40293; G05B 2219/40296; A61D 3/00; A61D 99/00; A61D 2003/006; H05G 1/00; H05G 1/02; H05G 1/04
USPC .......... 378/4, 17, 20, 91, 189, 190, 192–197, 378/203–205, 208, 210
See application file for complete search history.

(56) References Cited

U.S. PATENT DOCUMENTS

| 4,961,208 | A | * | 10/1990 | Okada | ...................... | A61B 6/04 250/363.04 |
| 5,574,763 | A | * | 11/1996 | Dehner | ................... | A61B 6/032 378/17 |

(Continued)

FOREIGN PATENT DOCUMENTS

WO    2013188617 A1    12/2013

OTHER PUBLICATIONS

Duckjune Kim; Developing a Mobile X-Ray Imaging System for Diagnosis Using LabVIEW Software and NI Hardware; Case Study by National Instruments; 2012; pp. 1-4; Korea.

*Primary Examiner* — Anastasia Midkiff
(74) *Attorney, Agent, or Firm* — Boyle Fredrickson, S.C.

(57) ABSTRACT

A CT machine for scanning a stationary patient may provide for two-bar linkage articulated arms to move a CT gantry in an arbitrary trajectory. In one embodiment, the gantry may fit within a cavity to expose a central platform, which may support a patient for vertical scans in which the gantry housing rises from the cavity after the patient is so positioned.

20 Claims, 4 Drawing Sheets

(56) References Cited

U.S. PATENT DOCUMENTS

| | | | |
|---|---|---|---|
| 7,388,941 B2 * | 6/2008 | Sukovic | A61B 6/032 378/19 |
| 8,505,137 B1 | 8/2013 | Gaines, Jr. | |
| 2008/0118035 A1 | 5/2008 | Maschke et al. | |
| 2010/0080349 A1 * | 4/2010 | Kalender | A61B 5/704 378/37 |
| 2011/0280379 A1 * | 11/2011 | Maschke | A61B 6/4411 378/196 |
| 2014/0139215 A1 * | 5/2014 | Gregerson | A61B 6/04 324/309 |

* cited by examiner

CT MACHINE FOR MULTI-ANGLE SCANNING OF STATIONARY PATIENTS

STATEMENT REGARDING FEDERALLY SPONSORED RESEARCH OR DEVELOPMENT

—

CROSS REFERENCE TO RELATED APPLICATION

—

BACKGROUND OF THE INVENTION

The present invention relates to computed tomography machines, and in particular to a gantry support structure allowing scanning of stationary patients.

Computed tomography (CT), and in particular computer x-ray tomography, is an imaging technique that may generate cross-sectional images of a patient by mathematically combining multiple x-ray images (projections) taken along the plane of the cross-section at a range of angles.

In fan beam CT, the x-rays used to acquire the projections are collimated to a thin fan beam lying within the plane of the cross-section and received by a narrow linear detector. The combination of the x-rays to a fan beam permits data acquisition with substantially reduced x-ray scatter, in turn providing improved image fidelity in the cross-sectional or tomographic image when compared to a comparable CT system using a cone beam of x-rays measured with an area detector array.

Generating a tomographic image normally requires a projection set of multiple projections over at least 180 degrees and preferably 360 degrees of angular range about the patient. The patient may be moved through a gantry holding an x-ray source and x-ray detector as they turn in opposition about the patient to acquire each x-ray projection set, either continuously during the orbital motion (helical scanning) or stepwise in between orbits (step scanning) to obtain x-ray projection sets for adjacent cross-sectional images that together describe a volume of tissue. Movement of the patient may be provided by supporting the patient supine on a horizontally extending radio translucent table that may move through the gantry.

The fan beams may generate cross-sectional images of "slices" that may be as thin as a few millimeters. Generating tomographic data for a significant volume of tissue in a reasonable time therefore requires rapid movement of the x-ray tube and detector in many orbits. For this reason CT acquisition normally use a specialized gantry system having a housing internally supporting the x-ray tube and detector on a bearing system for continuous or near continuous rotation about an unobstructed bore volume. This gantry system is readily distinguishable from typical C-arm systems used, for example, for general-purpose x-ray imaging and cone beam CT where only one or few orbits of the patient is required.

CT imaging of some patients may preferably be performed with the patient in a standing position. For example, a lung cancer patient undergoing thoracic radiotherapy may prefer to be in a standing position so as not to promote the coughing that often accompanies this treatment. Some medical conditions such as vertebral fractures may be more evident in a weight-bearing standing position.

Conventional CT systems employing a horizontally extending table generally prevent practical use of CT machines for large animals such as horses. While specialized tables may be constructed for horses, for example, as described in U.S. Pat. No. 8,505,137, positioning a large animal on such a table requires induction of general anesthesia, which substantially increases the amount of time required to obtain a scan.

SUMMARY OF THE INVENTION

The present invention positions a conventional high-speed CT annular gantry for support on motorized arms which may move the gantry in an arbitrary trajectory with respect to a stationary patient, eliminating the need to move the patient or enforce a horizontal patient orientation. In one embodiment, identical flanking two-link arms are provided, each presenting an articulated two-bar linkage having three parallel axes. A three-axis arm provides the ability to move the annular gantry in an arbitrary linear trajectory with vertical or horizontal scanning of stationary subjects in a variety of modes.

In one embodiment, the annular gantry may fit within a recessed pocket flush with a support platform allowing positioning of the patient without interference on the support platform and then elevating the gantry for a vertical scan.

Specifically, in a first embodiment, the invention may provide a computed tomography machine having a gantry holding an x-ray source and x-ray detector opposed across an opening through which a subject may be imaged as received along a first axis, the gantry including an actuator moving the x-ray source and x-ray detector in orbit about the first axis. The gantry may be held by a first and second support arm, each providing an articulated linkage of a forearm and upper arm, the latter mutually attached at an elbow joint that is positionable through a range of elbow angles about a second axis perpendicular to the first axis.

The distal ends of the forearms may attach to opposite sides of the gantry at wrist joints, the latter joining the forearms to the gantry and positionable at a range of wrist angles about a third axis parallel to the second axis. In addition, proximal ends of the upper arms may be attached to shoulder mounts at joints positionable at a range of shoulder angles about a fourth axis parallel to the second axis. The shoulder mounts may be adapted to attach to a stationary structure and motor actuators may provide position control of the elbow, wrist, and shoulder angles.

It is thus a feature of at least one embodiment of the invention to provide a mechanical structure that may move a gantry in a variety of trajectories for scanning of the stationary patient.

The trajectory may be a substantially straight line.

It is thus a feature of at least one embodiment of the invention to provide standard straight-line trajectories without the need for a linear carriage or the like.

The first and second al in may provide only two links and three mutually parallel axes.

It is thus a feature of at least one embodiment of the invention to provide an extremely simple linkage that is relatively easy to control and to manufacture.

The forearm and upper arm may be substantially equal in length.

It is thus a feature of at least one embodiment of the invention to provide arms that maximize achievable trajectory length.

The gantry support may provide a toroidal housing enclosing the x-ray source and x-ray detector during movement of the x-ray source and detector.

It is thus a feature of at least one embodiment of the invention to work with the standard CT gantry, which shields the moving x-ray tube and detector from possible contact with the patient such as allows more rapid scanning movement.

The x-ray source may produce a fan beam of x-rays extending a plane substantially perpendicular to the first axis and the x-ray detector may provide an arcuate detector array within the plane of substantially constant radius to the first axis.

It is thus a feature of at least one embodiment of the invention to permit the use of a fan-beam architecture for high resolution imaging.

The second axis of the wrist joints may substantially intersect the first axis of the gantry at right angles.

It is thus a feature of at least one embodiment of the invention to provide a balanced construction reducing torque on the wrist joints for different trajectories.

The opening through which a subject to be imaged may be received has an unobstructed diameter of greater than 25 inches.

It is thus a feature of at least one embodiment of the invention to provide a full function CT system capable of scanning humans and large animals.

The machine may include a camera system communicating with the electronic computer, providing images of a patient, and communicating with the electronic computer to detect when the patient is not fully within a swept volume of the opening along the trajectory.

It is thus a feature of at least one embodiment of the invention to provide collision detection for practical movement of the CT gantry about a stationary patient possibly unconstrained by a typical horizontal table or the like.

The camera system may communicate with the electronic computer and a display to provide an image on the display representing a swept volume of the opening superimposed upon an image of the patient from at least one camera of the camera system.

It is thus a feature of at least one embodiment of the invention to simplify positioning of the gantry for unusual scan trajectories based on a particular patient, for example, the head of a standing horse.

In one embodiment, the invention may provide a floor structure providing a horizontal surface for supporting a standing patient on a platform element and a cavity surrounding the platform element sized to receive the gantry therein beneath the horizontal surface with the first axis oriented vertically.

It is thus a feature of at least one embodiment of the invention to provide a machine that allows patient positioning on the floor without the need to climb over the gantry structure.

These particular objects and advantages may apply to only some embodiments falling within the claims and thus do not define the scope of the invention.

DETAILED DESCRIPTION OF THE PREFERRED EMBODIMENT

Figure 1:
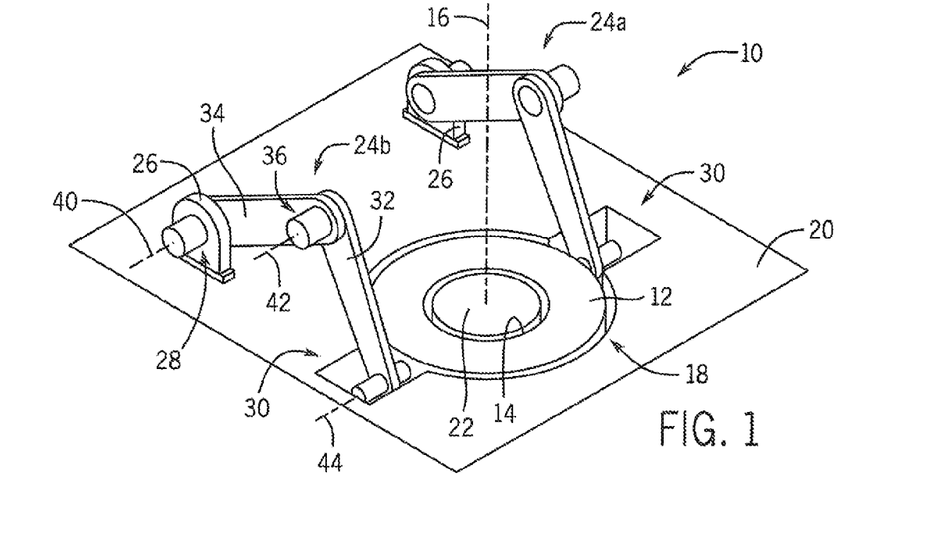
FIG. 1 is a perspective view of a first embodiment of the invention showing a gantry in a retracted position beneath the floor providing an exposed support platform, the gantry ring support held on opposed two-bar linkage arms.

Referring now to FIG. 1, a CT system 10 of the present invention may provide for a gantry 12 being generally a cylindrical toroid and having a central cylindrical bore 14 oriented along a central axis 16 of that cylindrical bore 14. The bore 14 may have a diameter of substantially greater than 25 inches to allow it to fit around a portion of the patient to be imaged.

As depicted, the gantry 12 may rest within a toroidal cavity 18 conforming generally to the outer dimensions of the gantry 12 so that an upper surface of the gantry 12 may lie substantially flush with a horizontal floor surface 20. As so positioned, the cylindrical bore 14 of the gantry 12 is filled by a central cylindrical platform 22 which extends upward through the bore 14 to the level of the floor surface 20 to provide a substantially continuous planar floor formed from the floor surface 20, the upper toroidal base of the gantry 12 and the platform 22.

A pair of floor supports 26 may be fixed with respect to the floor surface 20 on either side of the gantry 12 and displaced to one edge of the gantry 12. Motorized articulated arms 24a and 24b are attached to the floor support 26 at motorized shoulder joints 28 at proximate ends of the articulated arms 24a and 24b. The distal ends of the articulated arms 24a and 24b attach on diametrically opposite sides of the gantry 12 at motorized wrist joints 30.

Each of the articulated arms 24 may provide a substantially straight upper arm 34 attached by a motorized elbow joint 36 to a substantially straight forearm 32 of equal or unequal length to the upper arm 34. The motorized shoulder joints 28 allow each upper arm 34 to pivot with respect to the floor about a common horizontal axis 40 substantially perpendicular to axis 16. Likewise the motorized elbow joints 36 allow each forearm 32 to pivot with respect to each upper arm 34 about a common substantially horizontal axis 42 parallel to axis 40. Finally, the motorized wrist joints 30 allow the gantry 12 to pivot about an axis 44 with respect to the forearms 32.

Each of the motorized shoulder joint 28, elbow joint 36 and wrist joint 30 may, for example, include a gear motor and encoder combination to provide for position control of the relative angles of joints as is understood in the art.

Figure 2:
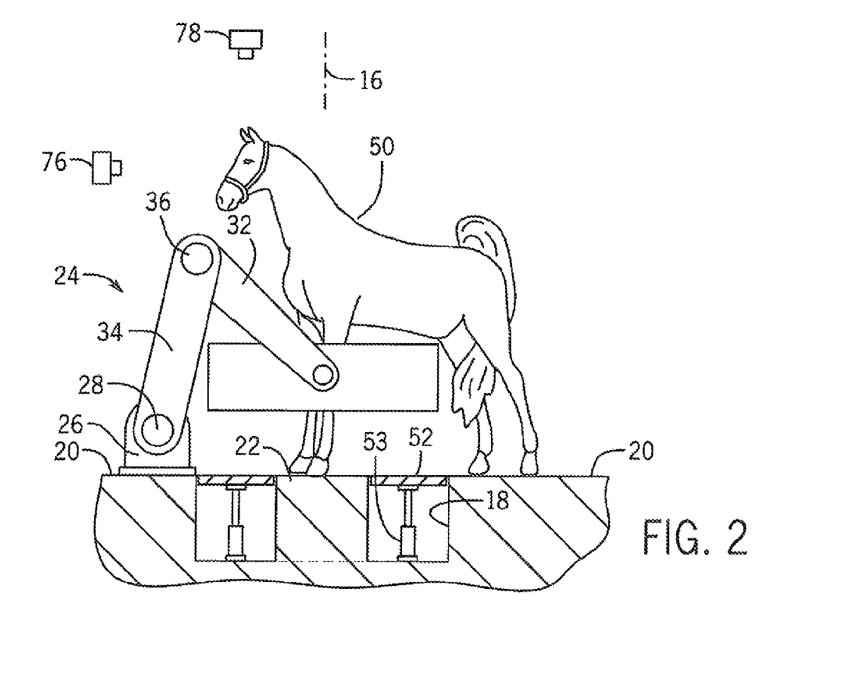
FIG. 2 is a side elevational view of the gantry of FIG. 1 as elevated about the front legs of a horse standing on the support platform during elevation of the gantry.

Referring now to FIG. 2, the upper face of the support platform 22 may provide a support for the thoracic limbs of a large animal such as a horse 50 which may be positioned to stand on the platform 22 when the gantry 12 is received within the cavity 18 and is substantially flush with the floor surface 20. The pelvic limbs of the horse 50 in this embodiment may be supported directly on the floor surface 20 outside of the area of the upper toroidal base of the gantry 12.

The arms 24 may then be operated to raise the gantry 12 in a substantially vertical direction with the axis 16 of the gantry 12 retained in a vertical direction to provide a scanning of a length of the thoracic limbs of the horse 50. It will be appreciated that positioning of the horse 50 before the scan is simplified by the fact that the horse is presented with a flat surface and need not step over or down onto another structure.

As the gantry 12 is raised, an annular cavity shield 52 may rise from within the cavity 18 to a level substantially flush with the floor surface 20 to prevent the open cavity from providing any hazard. This raising of the shield 52 may be accomplished, for example, with a telescoping hydraulic piston 53 or other methods well known in the art.

Figure 3:
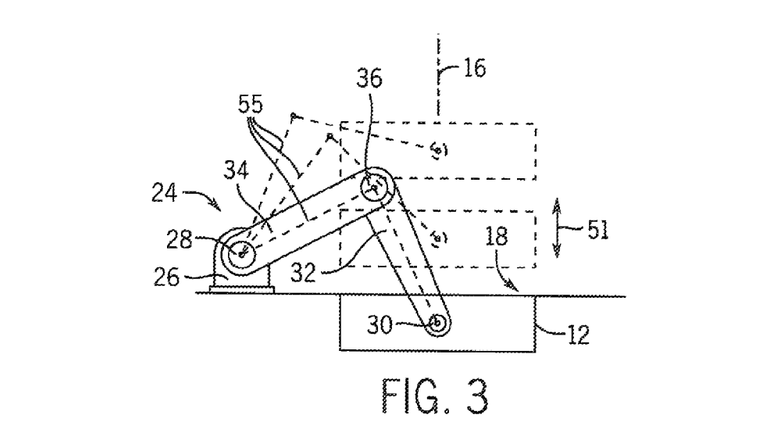
FIG. 3 is a simplified view of the gantry of FIG. 2 showing motion of the arms in elevating the gantry along the vertical trajectory of FIG. 2.
Figure 4:
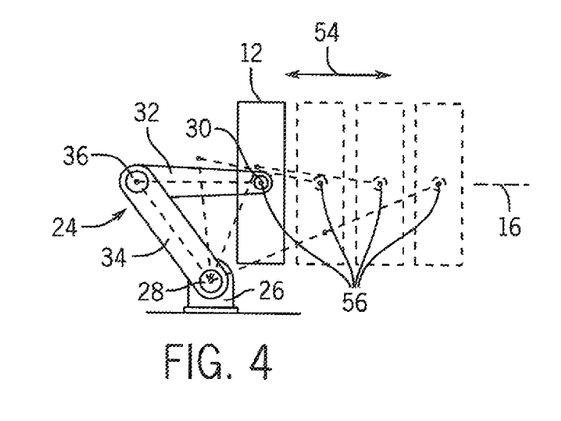
FIG. 4 is a view similar to that of FIG. 3 showing motion of the arms for a horizontal scanning trajectory.

Referring now to FIG. 3, it will be appreciated that the gantry 12 may move to follow a substantially vertical trajectory while maintaining the axis 16 vertically by a combined motion of the two-bar linkage formed by the forearm 32 and upper arm 34. This linear vertical trajectory 51 is provided by rotation of the shoulder joint 28 in a counterclockwise direction (as depicted in FIG. 4) to raise the wrist joint 30 with simultaneous extension of the forearm 32 of the arm 24 by straightening of the elbow joint 36 as the gantry 12 rises and a countervailing clockwise rotation of the wrist joint 30 to maintain the vertical orientation of the axis 16. By simultaneous movement of these joints through multiple positions 55, the need for a more complex arm with additional joints is avoided as well as bulky mechanisms that provide for linear tracks or the like.

Referring now to FIG. 4, this same architecture of arms 24 may be used to provide for a horizontal straight-line trajectory 54. After withdrawal of the gantry 12 from the cavity 18, the gantry 12 may be rotated until the gantry axis 16 is in a horizontal orientation with the upper arm 34 retracted in a counterclockwise direction and the forearm 32 lowered in a clockwise direction. At this point the scan may be started by rotating the upper arm 34 in a clockwise direction with countervailing rotation of the forearm 32 in the counterclockwise direction straightening the arm through elbow joint 36 and providing a slight counterclockwise rotation of the wrist joint 30 to maintain the position of the gantry 12 with the axis 16 horizontal through multiple positions 56 of the arms 24.

Figure 5:
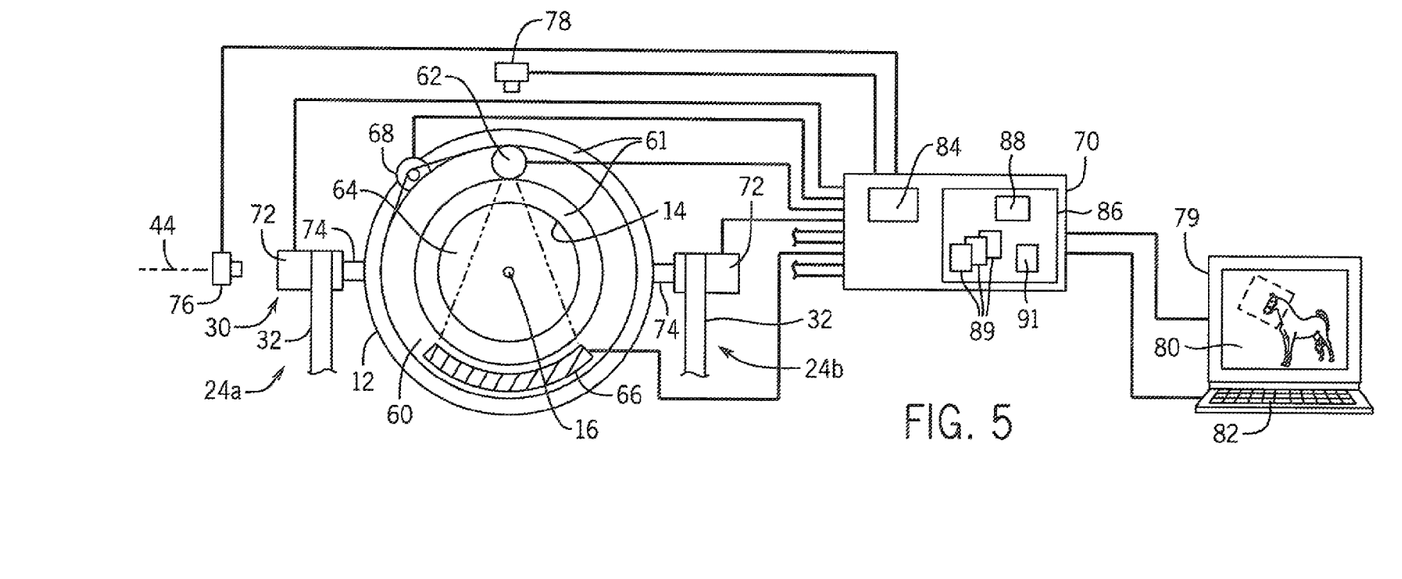
FIG. 5 is a block diagram of the CT system showing the principal controlled elements as attached to a controller.

Referring now to FIG. 5, the gantry 12 may hold a support ring 60 rotatable on a gantry frame 61. The support ring 60 may be held within gantry 12, for example, on roller bearings or the like positioned between the support ring 60 and the gantry frames 61. Attached to the support ring 60 in diametric opposition are an x-ray tube 62 and a linear detector array 66, the x-ray tube 62 providing an x-ray source and projecting a fan beam 64 of x-rays across the bore 14 to the linear detector array 66. The fan beam 64 extends generally within a plane perpendicular to the axis 16 diverging from a point at the x-ray tube 62 to be received by the linear detector array 66 extending within the plane along an arc of constant radius about axis 16.

During rotation of the support ring 60, the x-ray tube 62 and linear detector array 66 are preferably wholly enclosed within the housing of the gantry 12 to prevent risk of collision with the patient caused by rapid movement of the support ring 60. Rotation of the support ring 60 with respect to the gantry 12 may be provided by a rotational motor 68 held within the gantry 12 and communicating with a central controller 70 to be discussed below.

The x-ray tube 62 and linear detector array 66 also communicate with the controller 70 which may activate the x-ray tube 62 and collect the tomographic projections from the linear detector array 66 by rotation of the support ring 60 by control of rotational motor 68.

As noted above, the gantry 12 and in particular the gantry frame 61 is supported by the arms 24 at wrist joints 30. The wrist joints 30 each may include a gear motor/encoder pair 72 attached by shaft 74 to diametrically opposite points on the gantry frames 61 along common axis 44 shared by the arms 24a and 24. These gear motor/encoder pairs 72 provide encoder signals to the controller 70 indicating the angle of the wrist joints 30 and receive command signals therefrom controlling actuation of the gear motor. In this way, the controller 70 may control the positioning of the wrist joints 30.

The shoulder joints 28 and elbow joints 36 likewise have similar gear motor encoders (not shown in FIG. 5) also in communication with the controller 70 for angle control of these joints.

The controller 70 may also communicate with a camera system including a horizontal camera 76 and vertical camera 78 positioned to obtain an elevational image and plan image of a region occupied by the patient through which the gantry 12 may move as will be discussed below. The controller 70 may also communicate with a graphic display terminal 79 for providing output images 80 such as tomographic images, positioning information, and user input devices such as a keyboard 82 of the type generally known in the art for receiving instructions from the user, for example, for positioning the gantry 12.

The controller 70 may employ a general computer architecture including one or more processors 84 communicating with a memory 86 for the storage of non-transient control programs 88 as will be discussed below and for storage of tomographic projection sets 89 and resulting tomographic images 91 generated by filtered back projection or the like also implemented by the control program 88.

Referring again to FIGS. 2-4, during a tomographic acquisition, the controller 70 may control the joints 28, 36 and 30 to effect the desired trajectory 54 or 51 or any other trajectory cursed or straight within the range of the arms 24. These trajectories are implemented by a series of motions of the joints as will be understood to those of ordinary skill in the art and as may be calculated using the known geometry of the arms 24. At various locations or continuously with movement along trajectory 54, the x-ray tube 62 and linear detector array 66 on the support ring 60 may be rotated, generally by 180 degrees plus the fan beam angle or more, to obtain a tomographic projection set for that location. A set of tomographic projection sets 89 may thereby be obtained which may be reconstructed into a tomographic image 91. Multiple sets of tomographic projection sets 89 may be used to provide images over a volume of the patient.

Figures 6, 7, 8:
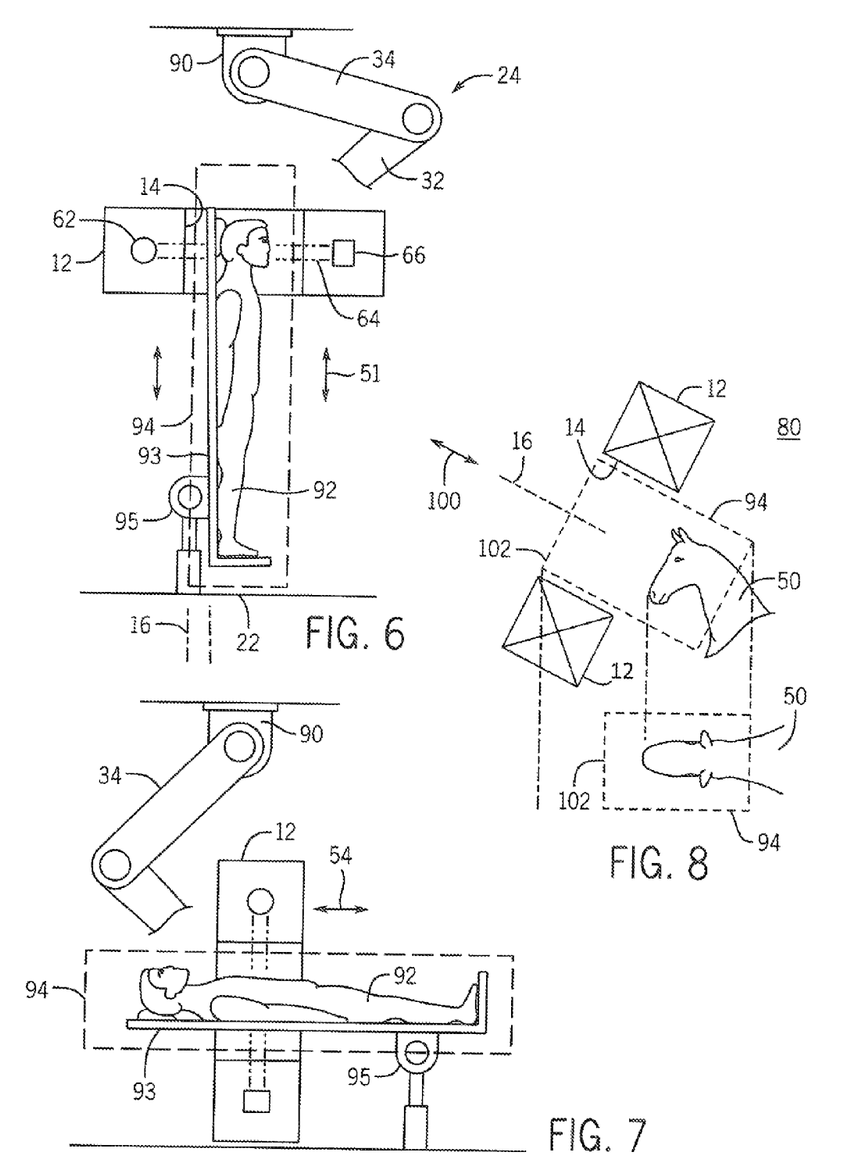
FIG. 6 is a side elevational view of the invention as attached to a ceiling support for scanning a substantially vertical patient held on a patient table supported on the support platform.
FIG. 7 is a figure similar to FIG. 6 showing a horizontal scanning of the gantry as attached to the ceiling support.
FIG. 8 is a representation of a display generated by the controller showing a swept volume of the gantry for an anticipated trajectory used for preventing collision of the moving gantry with a stationary patient.

Referring now to FIG. 6, it will be appreciated that the floor support 26 may be replaced with ceiling supports 90, for example, attached to supporting truss structures in the ceiling, so that the arms 24 extend downward from the ceiling. Like the floor support 26, the ceiling supports 90 may provide for movement of the upper arms 34 about a common axis 40 now displaced toward the ceiling using gear motor/encoder combinations. In this configuration, the gantry 12 may be stowed against the ceiling out of the way when it is not in use providing additional floor area for other activities. Vertical scans of the patient 92, such as of a person, may be provided where the person stands on a support platform 22 or is supported against a vertical radiolucent support 93 positioned within a swept volume 94 of the bore 14 during motion in a vertical trajectory 51. In this case the trajectory may pass downward and then upward in the apposite sequence described with respect to FIG. 2.

In order to limit motion of the patient 92, the surface of the vertical table 93 may slope slightly backward from vertical so that the patient 92 may lean against that surface for support better immobilizing them during the acquisition process.

Referring to FIG. 7, same system may be used with the table 93 rotated about a rotational joint 95 to a horizontal position. Here the gantry 12 moves along the horizontal trajectory 54 described generally with respect to FIG. 4 but as supported with the ceiling support 90 on the ceiling.

Referring now to FIG. 8, motion of the arms 24 can be used to scan the gantry 12 along an arbitrary angled trajectory 100, angled with respect to horizontal and vertical, to allow, for example, scanning of the head of a standing horse 50. By being able to adjust the trajectory 100, the gantry 12 may be positioned about a head to look for jaw, mouth, sinus, nasal passage, guttural pouch, or teeth problems.

Motion of the gantry 12 with respect to a patient, where the patient is not necessarily supported or restrained on the table, is facilitated by the camera system of cameras 76 and 78 which may provide an image 80 depicting the gantry 12, for example, diagrammatically and may superimpose on that image 80 a computer-generated swept volume 94 of the bore 14 as it moves along a planned trajectory 100 within the range of the arms 24. The image 80 may present a bounding box 102 circumscribing the swept volume 94, for example, in side elevation and top plan view, as shown, to allow rapid confirmation of the positioning of the gantry 12 prior to the scan. The same signals from the cameras 76 and 78 may also be used to monitor the trajectory 100 to prevent collision with the patient during the scan. Touch sensitive switches or other proximity switches may be incorporated into the edges of the gantry 12 to guard against unintended contact with the patient.

Figure 9A:
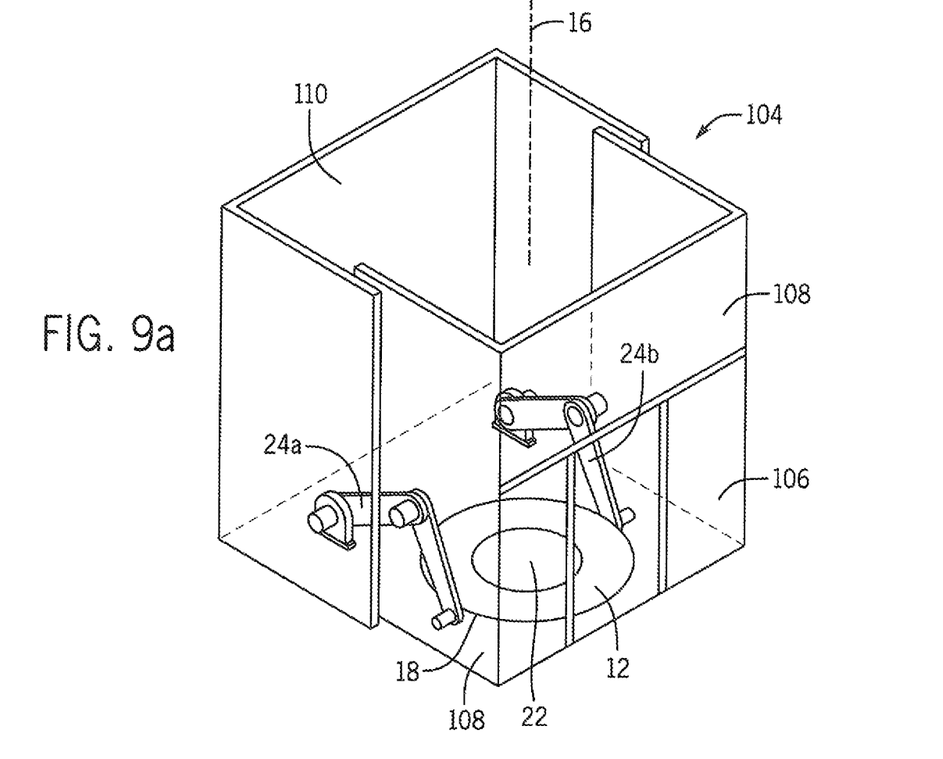
FIGS. 9a and 9b are perspective and top plan views of a radiation shielding enclosure possible with the present invention.
Figure 9B:
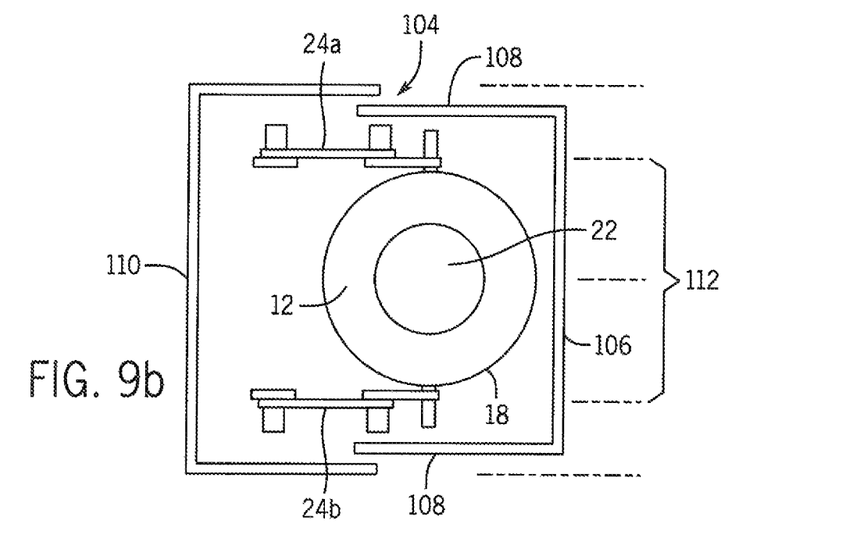

Referring now to FIGS. 9a and 9b, the ability to track a vertical trajectory along axis 16 with the gantry 12 allows an extremely compact radiation shielding structure 104 to be provided comprising an upstanding front wall 106 and flanking connected sidewalls 108 closely proximate to the cavity 18 on three sides and a rear wall 110 displaced from the cavity 18 by an amount necessary for free operation of the arms 24a and 24b. Generally, the front wall 106 and sidewalls 108 may be within two diameters 112 of the gantry 12 from the center of the platform 22, greatly reducing the amount of material necessary for these walls and the size of the radiation shielding structure 104.

The radiation shielding structure 104 may be such as to shield operators from incidental radiation from the operation of the CT system 10 and may include, or be substantially entirely, leaded glass or plastic to reduce any sense of claustrophobia by a patient standing on the platform 22. The radiation shielding structure 104 may be mounted on casters or glides or other mechanisms to allow repositioning of these radiation shielding structures 104 as necessary for different imaging purposes. In this way, the relatively large shielded room may not be required.

It will be appreciated that the present invention may be used in a variety of imaging circumstances including imaging of leg joints, hips, and the spine in weight-bearing configuration to determine bone degeneration or spine disorders such as scoliosis. CT angiography with the patient in the vertical position may be used to examine the arteries for narrowing or aneurysms that may become more pronounced and when viewed if the patient supine.

The term patient as used herein is intended to include both human and animal patients.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A computed tomography machine comprising:
   a gantry holding an x-ray source and x-ray detector opposed across an opening through which a subject to be imaged may be received along a first axis, the gantry including an actuator for moving the x-ray source and x-ray detector in orbit about the first axis;
   a first support arm and a second support arm, each providing an articulated linkage of a forearm and upper arm mutually attached at an elbow joint positionable through a range of elbow angles about a second axis perpendicular to the first axis;
   wherein distal ends of the forearms are attached to opposite sides of the gantry at wrist joints joining the forearms to the gantry and positionable at a range of wrist angles about a third axis parallel to the second axis;
   wherein proximal ends of the upper arms are attached to shoulder mounts at joints positionable at a range of shoulder angles about a fourth axis parallel to the second axis, the shoulder mounts adapted to attach to a stationary structure; and
   motor actuators providing position control of the elbow, wrist, and shoulder angles.

2. The computed tomography machine of claim 1 further including an electronic computer executing a program stored in non-transient memory to move the gantry along a trajectory while acquiring x-ray data.

3. The computed tomography machine of claim 2 wherein the trajectory is a substantially straight line.

4. The computed tomography machine of claim 1 wherein the first and second arms provide only two bar linkage and three mutually parallel axes.

5. The computed tomography machine of claim 4 wherein the forearm and upper arm are substantially equal in length.

6. The computed tomography machine of claim 1 wherein the gantry provides a toroidal housing enclosing the x-ray source and x-ray detector during movement of the x-ray source and detector.

7. The computed tomography machine of claim 1 wherein the x-ray source produces a fan beam of x-rays extending in a plane substantially perpendicular to the first axis and the x-ray detector provides an arcuate detector array within the plane and at a substantially constant radius.

8. The computed tomography machine of claim 1 wherein a second axis of the wrist joints substantially intersects the first axis of the gantry at right angles.

9. The computed tomography machine of claim 1 in which the opening through which a subject to be imaged may be received has an unobstructed diameter of greater than 25 inches.

10. The computed tomography machine of claim 1 further including an electronic computer executing a program stored in non-transient memory to move the gantry along a trajectory while acquiring x-ray data and further including a camera system communicating with the electronic computer, the camera system providing images of a patient and communicating with the electronic computer to detect when a patient being scanned is not fully within a swept volume of the opening along the trajectory.

11. The computed tomography machine of claim 1 further including an electronic computer executing a program stored in non-transient memory to move the gantry along a trajectory while acquiring x-ray data and further including a camera system communicating with the electronic computer and a display to provide an image on the display representing a swept volume of the opening superimposed upon an image of the patient from at least one camera of the camera system.

12. A computed tomography machine comprising:
a gantry providing an x-ray source and x-ray detector opposed across an opening through which a subject to be imaged may be received along a first axis, the gantry including an actuator for rotating the x-ray source and x-ray detector in orbit about the first axis;
a floor structure providing a horizontal surface for supporting a standing patient on a platform element and providing a cavity surrounding the platform element receiving the gantry therein beneath the horizontal surface with the first axis oriented vertically;
a first support arm and a second support arm, each attached to opposite sides of the gantry between the gantry and a floor mounts and including actuators for moving the first and second support arms to raise the gantry from the cavity about the platform element and a patient supported on the platform element; and
and electronic computer executing a program stored in non-transient memory to move the gantry along a trajectory while acquiring x-ray data with the x-ray source and x-ray detector.

13. The computed tomography machine of claim 12 wherein the gantry provides a toroidal housing enclosing the x-ray source and x-ray detector during movement of the x-ray source and detector.

14. The computed tomography machine of claim 12 wherein the x-ray source produces a fan beam of x-rays extending along a plane substantially perpendicular to the first axis and the x-ray detector provides an arcuate detector array within the plane and at a substantially constant radius.

15. The computed tomography machine of claim 12 wherein the first and second arms are attached to rotate the gantry along an axis substantially intersecting the first axis of the gantry at right angles.

16. The computed tomography machine of claim 12 in which the opening through which a subject to be imaged may be received has an unobstructed diameter of greater than 25 inches.

17. The computed tomography machine of claim 1 further including a vertically extending radiation shielding wall positioned proximate to the cavity and substantially surrounding the cavity.

18. A method of providing a CT scan of a stationary patient using a computed tomography machine having;
a gantry providing an x-ray source and x-ray detector opposed across an opening through which a subject to be imaged may be received along a first axis and including an actuator to move the x-ray source and x-ray detector in orbit about the first axis;
a floor structure providing a horizontal surface for supporting a standing patient on a platform element and providing a cavity surrounding the platform element receiving the gantry therein beneath the horizontal surface with the first axis oriented vertically;
a first support arm and a second support arm, each attached between opposite sides of the gantry and a floor mounts and including actuators for moving the first and second support arms to raise the gantry from the cavity about the platform element and a patient supported on the platform element; and
electronic computer executing a program stored in non-transient memory to move the gantry along a trajectory while acquiring x-ray data with the x-ray source and x-ray detector;
the method comprising the steps of:
(a) with the gantry within the cavity, positioning the patient on the platform element with a region of interest extending substantially upward therefrom within a volume directly above the platform element; and
(b) executing the program on the electronic computer to raise the gantry from the cavity in a trajectory along the region of interest to collect tomographic projections set.

19. The method of claim 18 wherein the gantry provides a toroidal housing enclosing the x-ray source and x-ray detector during movement of the x-ray source and detector.

20. The method of claim 18 herein the x-ray source produces a fan beam of x-rays extending along a plane substantially perpendicular to the first axis and the x-ray detector provides an arcuate detector array within the plane and at a substantially constant radius.

* * * * *